United States Patent [19]

Pazirandeh et al.

[11] Patent Number: 5,824,512
[45] Date of Patent: Oct. 20, 1998

[54] BACTERIA EXPRESSING METALLOTHIONEIN GENE INTO THE PERIPLASMIC SPACE, AND METHOD OF USING SUCH BACTERIA IN ENVIRONMENT CLEANUP

[75] Inventors: Mehran Pazirandeh, Silver Spring; James R. Campbell, Olney, both of Md.

[73] Assignee: The United States of America as represented by the Secretary of the Navy, Washington, D.C.

[21] Appl. No.: 754,431

[22] Filed: Nov. 22, 1996

[51] Int. Cl.$^6$ .............................. C12P 21/06; C12N 1/20; C07H 17/00; C07K 14/00
[52] U.S. Cl. ..................... 435/69.7; 435/252.33; 435/252.3; 530/350; 536/23.4
[58] Field of Search .................... 435/69.7, 243, 435/252.3, 252.33, 320.1; 530/350; 536/23.4

[56] References Cited

U.S. PATENT DOCUMENTS 5,500,353  3/1996  Smit et al. ............................. 435/69.1
5,516,697  5/1996  Kruzel ....................................... 436/84

OTHER PUBLICATIONS

Pazirandeh et al. Dec. 1995 43(6):1112–1117.
Jacobs et al. 1989 Gene 83:95–103.
Maina et al. 1988 Gene 74:365–373.

*Primary Examiner*—Karen Cochrane Carlson
*Attorney, Agent, or Firm*—Thomas McDonnell; Barry Edelberg

[57] ABSTRACT

A gene coding for the expression of metallothionein is incorporated into an expression vehicle for expressing the metallothionein gene into the periplasmic space of a bacterium including the expression vehicle. It may also be possible to incorporate multiple copies of the metallothionein gene within a single bacterium. One typical expression vehicle is a p-MalP plasmid constructed to include the metallothionein gene. Using this expression vehicle, one can induce bacteria, such as transformed *E. coli*, to express metallothionein into the periplasmic space as a fusion product with, for example, the maltose-binding protein. Killed cell that have expressed metallothionein into the periplasmic space may then be attached to a solid support. The resulting device may be used to remove heavy metals from aqueous media.

12 Claims, 3 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 96 base pairs
        ( B ) TYPE: nucleic acid
        ( C ) STRANDEDNESS: single stranded
        ( D ) TOPOLOGY: circular     ( i i i ) HYPOTHETICAL: no     ( i v ) ANTI-SENSE: no     ( x i ) SEQUENCE DESCRIPTION: SEQ ID NO: 1:

```
GAGGGAAGGA  TTTCAGAATT  CGGATCC  TGT  GGT  TGC  TGT  GGC  AAA  GGT  CAT  GGT  GGC   57
                                 Cys  Gly  Cys  Cys  Gly  Lys  Gly  His  Cys  Gly
                                  1                   5                        10

TGT  TGC  GGC  AAA  GGT  CAC  TGC  GGT  TGC  TGT  GGT  AAGCTT                        96
Cys  Cys  Gly  Lys  Gly  His  Cys  Gly  Cys  Cys  Gly
           15                              20
```

( 2 ) INFORMATION FOR SEQ ID NO:2:

( i ) SEQUENCE CHARACTERISTICS:
        ( A ) LENGTH: 96 base pairs
        ( B ) TYPE: nucleic acid
        ( C ) STRANDEDNESS: single stranded
        ( D ) TOPOLOGY: circular   ( i i i ) HYPOTHETICAL: no     ( i v ) ANTI-SENSE: no     ( x i ) SEQUENCE DESCRIPTION: SEQ ID NO:2:

```
GAGGGCAGGA TTTCAGAATT CGGATCC TGT GGT TGC TGT GGC AAA GGT CAT GGT GGC    57
                                Cys Gly Cys Cys Gly Lys Gly His Gly Gly
                                 1           5                       10
TGT TGC GGC AAA GGT CAC TGC GGT TGC TGT GGT AAGCTT                         96
Cys Cys Gly Lys Gly His Cys Gly Cys Cys Gly
             15                      20
```

( 2 ) INFORMATION FOR SEQ ID NO:3:

( i ) SEQUENCE CHARACTERISTICS:
        ( A ) LENGTH: 48 base pairs
        ( B ) TYPE: nucleic acid
        ( C ) STRANDEDNESS: single stranded
        ( D ) TOPOLOGY: circular   ( i i i ) HYPOTHETICAL: no     ( i v ) ANTI-SENSE: no     ( x i ) SEQUENCE DESCRIPTION: SEQ ID NO:3:

```
GGTGACTGTG GTTGTTCTGG TGCCTCTTCT TGTAACTGTG GTTCTGGC                       48
```

( 2 ) INFORMATION FOR SEQ ID NO:4:

( i ) SEQUENCE CHARACTERISTICS:
        ( A ) LENGTH: 38 base pairs
        ( B ) TYPE: nucleic acid
        ( C ) STRANDEDNESS: single stranded
        ( D ) TOPOLOGY: circular   ( i i i ) HYPOTHETICAL: no     ( i v ) ANTI-SENSE: no     ( x i ) SEQUENCE DESCRIPTION: SEQ ID NO:4:

```
TGTTCTTGTT CTAACTGTGG CTCTAAATGA TAACTGCA                                  38
```

( 2 ) INFORMATION FOR SEQ ID NO:5:

( i ) SEQUENCE CHARACTERISTICS:
        ( A ) LENGTH: 39 base pairs
        ( B ) TYPE: nucleic acid
        ( C ) STRANDEDNESS: single stranded
        ( D ) TOPOLOGY: circular   ( i i i ) HYPOTHETICAL: no     ( i v ) ANTI-SENSE: no     ( x i ) SEQUENCE DESCRIPTION: SEQ ID NO:5:

```
ACAGTTACAA GAAGAGGCAC CAGAACAACC ACAGTCACC                                 39
```

( 2 ) INFORMATION FOR SEQ ID NO:6:

( i ) SEQUENCE CHARACTERISTICS:
        ( A ) LENGTH: 43 base pairs
        ( B ) TYPE: nucleic acid
        ( C ) STRANDEDNESS: single stranded (D) TOPOLOGY: circular (iii) HYPOTHETICAL: no (iv) ANTI-SENSE: no (xi) SEQUENCE DESCRIPTION: SEQ ID NO:6:

GTTATCATTT AGAGCCACAG TTAGAACAAG AACAGCCAGA ACC                43

(2) INFORMATION FOR SEQ ID NO:7:

(i) SEQUENCE CHARACTERISTICS:
    (A) LENGTH: 86 base pairs
    (B) TYPE: nucleic acid
    (C) STRANDEDNESS: single stranded
    (D) TOPOLOGY: circular (iii) HYPOTHETICAL: no (iv) ANTI-SENSE: no (xi) SEQUENCE DESCRIPTION: SEQ ID NO:7:

```
GGT  GAC  TGT  GGT  TGT  TCT  GGT  GCC  TCT  TCT  TGT  AAC  TGT  GGT        42
Gly  Asp  Cys  Gly  Cys  Ser  Gly  Ala  Ser  Ser  Cys  Asn  Cys  Gly
1                   5                        10

TCT  GGC  TGT  TCT  TGT  TCT  AAC  TGT  GGC  TCT  AAA  TGATAA               81
Ser  Gly  Cys  Ser  Cys  Ser  Asn  Cys  Gly  Ser  Lys
15                       20                       25

CTGCA                                                                       86
```

(2) INFORMATION FOR SEQ ID NO:8:

(i) SEQUENCE CHARACTERISTICS:
    (A) LENGTH: 96 base pairs
    (B) TYPE: nucleic acid
    (C) STRANDEDNESS: single stranded
    (D) TOPOLOGY: circular (iii) HYPOTHETICAL: no (iv) ANTI-SENSE: no (xi) SEQUENCE DESCRIPTION: SEQ ID NO:8:

```
TCGAGCTCGG  TACCCGGCCG  GGGATCC ATC GAG GGT AGG  CCTGAATTCA GTAAAACCCT      59
                                Ile Glu Gly Arg
                                  1

CGATGGATCC  TCTAGAGTCG  ACCTGCAGGC  AAGCTTG                                 96
```

(2) INFORMATION FOR SEQ ID NO:9:

(i) SEQUENCE CHARACTERISTICS:
    (A) LENGTH: 4 amino acids
    (B) TYPE: amino acid
    (D) TOPOLOGY: linear (xi) SEQUENCE DESCRIPTION: SEQ ID NO:9:

```
Ile  Glu  Gly  Arg
1
```

(2) INFORMATION FOR SEQ ID NO:10:

(i) SEQUENCE CHARACTERISTICS:
    (A) LENGTH: 21 amino acids
    (B) TYPE: amino acid
    (D) TOPOLOGY: linear (xi) SEQUENCE DESCRIPTION: SEQ ID NO:10:

| Cys | Gly | Cys | Cys | Gly | Lys | Gly | His | Cys | Gly | Cys | Cys | Gly | Lys | Gly | His |
| 1 | | | | 5 | | | | | 10 | | | | | 15 | |

| Cys | Gly | Cys | Cys | Gly |
|-----|-----|-----|-----|-----|
| | | | 20 | |

( 2 ) INFORMATION FOR SEQ ID NO:11:

( i ) SEQUENCE CHARACTERISTICS:
        ( A ) LENGTH: 25 amino acids
        ( B ) TYPE: amino acid
        ( D ) TOPOLOGY: linear     ( x i ) SEQUENCE DESCRIPTION: SEQ ID NO:11:

| Gly | Asp | Cys | Gly | Cys | Ser | Gly | Ala | Ser | Ser | Cys | Asn | Cys | Gly | Ser | Gly |
| 1 | | | | 5 | | | | | 10 | | | | | 15 | |

| Cys | Ser | Cys | Ser | Asn | Cys | Gly | Ser | Lys |
|-----|-----|-----|-----|-----|-----|-----|-----|-----|
| | | | 20 | | | | | 25 |

BACTERIA EXPRESSING METALLOTHIONEIN GENE INTO THE PERIPLASMIC SPACE, AND METHOD OF USING SUCH BACTERIA IN ENVIRONMENT CLEANUP

BACKGROUND OF THE INVENTION

1. Field of the Invention

The present invention relates generally to microorganisms that produce metallothioneins, and more specifically to recombinant metallothionein-producing microorganisms that have a high capacity for binding heavy metals at or near their cell walls, and immobilized biomasses obtained therefrom.

2. Description of the Background Art

The discharge of heavy metals into the environment due to agricultural, industrial, and military operations, and the effect of this pollution on the ecosystem is of great concern. Recent research in the area of heavy metal removal from waste waters and sediments has focused on the development of novel materials with increased affinity, capacity, and selectivity for target metals. One of the most selective heavy metal binding molecules is the family of small molecular weight proteins called metallothioneins (phytochelatins in plants). These proteins are cysteine-rich and bind heavy metals, such as cadmium, with very high affinity. Recently, the expression of the *N. crassa* metallothionein gene in *E. coli* and the ability of this recombinant *E. coli* (NCP) to sequester cadmium from solutions has been reported (Pazirandeh et al. *Appl. Microbio. Biotechnol.*, (1995) 43:1112–1117, the entirety of which is incorporated herein by reference for all purposes; M. Pazirandeh, (1996) *Biochem. and Molec. Biol. Intl.*, Vol. 39, NO. 4:789–795 the entirety of which is incorporated herein by reference for all purposes). These results demonstrated the ability of the recombinant *E. coli* expressing the metallothionein gene to sequester cadmium from solutions rapidly and with high selectivity. Although these results were encouraging, the development of a bacterial-based heavy metal biosorbent requires the bacteria to be immobilized, reusable, and able to sequester heavy metals from waste waters which are often contaminated with solvents and other toxic compounds (eg. polyaromatic hydrocarbons).

SUMMARY OF THE INVENTION

Accordingly, it is an object of this invention to remove heavy metal contaminants from waste waters and sediments.

It is another object of the present invention to provide an immobilized heavy metal biosorbent.

It is a further object of the present invention to provide an immobilized and reusable heavy metal biosorbent.

These and additional objects of the invention are accomplished by bacteria including a plasmid that expresses a metallothionein into the periplasmic space. After the metallothionein expression into the periplasmic space (typically by induction), cell fragments or whole killed cell (i.e., a nonviable biomass) may be immobilized to a solid support that is then contacted with the waste material. The metallothionein reversibly and specifically binds heavy metal contaminants. Removal of the solid support and attached biomass removes the bound heavy metal contaminants. The solid support/biomass structure may then be regenerated by removal of the bound heavy metals.

BRIEF DESCRIPTION OF THE DRAWINGS

A more complete appreciation of the invention will be readily obtained by reference to the following Description of the Preferred Embodiments, wherein.

DESCRIPTION OF THE PREFERRED EMBODIMENTS

A metallothionein gene useful according to the present invention may be obtained from any available source, natural and artificial. Naturally occurring metallothionein genes are found, for example, in *Neurospora crassa* and, along with its leadoff sequences, may be isolated by the use of appropriate restriction nucleases based upon the well known genome of that organism. The *Neurospora crassa* gene expressing the metallothionein protein, and its lead off sequences may also be synthesized using well-known DNA synthesis techniques. The inclusion of the leadoff sequences maintains the frame reference required for proper reading of the gene.

The metallothionein gene may be synthetic or natural, and may be a polymeric form of a monomer metallothionein gene, as well as a variant codon for amino acids have been replaced by codons for other amino acids to enhance metal uptake affinity and/or to obtain molecules that have an affinity for other heavy metals such as Ag, Au, or Cr. Also, synthetic sequences containing coding for various length polymers of Gly-Cys amino acid in orders such as (Gly- Cys-Gly-Cys) as well as addition sequences coding for amino acid patterns such as Cys-Gly-Cys-Cys-Gly-Lys-Gly-His-Cys-Gly-Cys-Gly-Lys-Gly-His-Cys-Gly-Cys-Cys-Gly may be incorporated into the sequence coding for metallothionein, typically at the portion of the gene coding for C terminus. Addition sequences may be added at the portion of the metallothionein gene coding for the N terminus in addition to or instead of the portions coding for the C-terminus. One typical addition sequence coding for the Cys-Gly-Cys-Cys-Gly-Lys-Gly-His-Cys-Gly-Cys-Gly-Lys-Gly-His-Cys-Gly-Cys-Cys-Gly is:

```
                                                  Cys—Gly—
GAG—GGA—AGG—ATT—TCA—GAA—TTC—GGA—TCC—TGT—GGT—

Cys   Cys   Gly   Lys   Gly   His   Cys   Gly   Cys   Cys
TGC—TGT—GGC—AAA—GGT—CAT—GGT—GGC—TGT—TGC—

Gly   Lys   Gly   His   Cys   Gly   Cys   Cys   Gly
GGC—AAA—GGT—CAC—TGC—GGT—TGC—TGT—GGT—AAG—CTT—
                                                        [SEQ ID NO:1]
```

Another useful addition sequence for the present invention is:

```
GAG—GGC—AGG—ATT—TCA—GAA—TTC—GGA—TCC—TGT—GGT—

TGC—TGT—GGC—AAA—GGT—CAT—GGT—GGC—TGT—TGC—GGC—

AAA—GGT—CAC—TGC—GGT—TGC—TGT—GGT—AAG—CTT—   [SEQ ID NO:2]
```

Except where indicated otherwise, in the present specification and the appended claims, the term "metallothionein" includes native and synthetic forms of the metallothionein protein, as well as metallothionein-derived molecules. Metallthionein-derived molecules include fusion products of metallothionein and another protein, metallothionein having addition sequences which give the final expressed molecule stablity and modifications used to improve the stablity and/or activity of the biosorbent product, such as heat treatment, treatment with metabolic inhibitors, treatment with dilute acid; fragments of metallothionein retaining metal binding activity fused with a Cys-Gly motif yielding a final metal binding motif which has an enhanced metal uptake profile and stability; polymers of metallothionein containing additional sequences that serve to enhance the heavy metal binding and allow the expression of multiple repetitive copies of a certain gene such as the metallothionein gene; and variants of metallothion that have had amino acid replacements to enhance stability and/or metal uptakes; and metallothionein proteins that have been modified in a way that they retain useful metal-binding capability.

Once the metallothionein gene, including any leadoff and addition sequences, has been synthesized and isolated, it is then cloned into an expression vector, such as a plasmid. One particularly suitable plasmid is the p-MalP expression vector. Preferably, multiple copies of the metallothionein gene are cloned into the plasmid. These genes should be cloned into the expression vector so that the metallothionein gene is expressed as a fusion product with a cell membrane protein. Typically, in the p-MalP expression vector, the metallothionein genes are cloned so as to use fusion with the maltose-binding protein as the mode for expression. This fusion assures that the metallothionein genes are expressed into the periplasmic space.

The recombinant expression vector may then be inserted into any host bacteria compatible with, and capable of expressing the metallothionein gene in that vector into the periplasmic space. *E. coli* is a particular useful host when the expression vector is a plasmid, such as the pMalP expression vector. The expression vector may be introduced into the host by any known means. Of course, plasmids, such as the pMalP expression vector, may be easily introduced into a *E. coli* by the commonly known process of transformation. In some cases, it may be possible to insert multiple copies of the recombinant expression vector into a single cell.

The transformed cell may then be isolated, for example by growth in luria media containing ampicillin (ampicillin or other antibiotic resistant genes are typically included in most plasmid expression vectors (such as pMalP) or by any other known means. These transformed cells may be induced to express metallothionein into the periplasmic space, then rendered nonviable. Transformed cell may be rendered nonviable by, for example, autoclaving at 212° C. or other standard autoclaving temperature for about 20 minutes (or other standard time), overnight heating in an oven at 100° C. (typically about 12 hours), incubation in about 1–5 mmol sodium azide for about 1 hour, uv radiation (for example by placing the bacteria in a laminar flow hood and exposing for several minutes, formaldehyde (for example 2% aq. solution), glutaraldehyde (for example 2% aq. solution. Glutaraldehyde may be particularly advantageous since it can simultaneously couple the bacteria to silica beads). Generally, the method by which the cells are killed is not critical to the present invention in its broadest sense, provided that the nonviable cells retain bound metallothionein available for binding to heavy metals. The nonviable cell are then attached to a variety of substrates such as alginate, acrylamide, or porous glass beads. Attachment of nonviable transformed cell to a solid support may be accomplished by any known method, such as absorption, encapsulation, or covalent attachment (for example treatment with glutaraldehyde). Kolot et al., *Immobilized Microbial Systems*:—Principle, Techniques and Industrial Applications, Robert E. Krieger Publishing Co., Malabar, Fla. (1988) (the entirety of which is incorporated herein by reference for all purposes) describes a variety well-known techniques useful for attaching a biomass made according to the present invention to a surface.

Typically, the metals for which metallothioneins have the highest affinity are Cd, Pb, Hg, Cu, and Zn. Metallothioneins also bind to other metals, such as Ni, but with lower affinity. The relative affinities of metallothioneins for specific metals may be varied somewhat by the inclusion of addition sequences and by the selection of the appropriate fusion partner.

Typical fusion partners include maltose-binding protein and outer membrane lipoprotein (pET-20 expression vector). Other fusion partners may be used.

Having described the invention, the following examples are given to illustrate specific applications of the invention including the best mode now known to perform the invention. These specific examples are not intended to limit the scope of the invention described in this application.

EXAMPLES

Example 1

Materials and Methods:

Materials:

Bacterial strains TB1 and expression plasmids pMal-c and pMal-p were from New England Biolabs. $^{109}$Cd was from New England Nuclear (specific activity 180 Ci/mole). Preformed SDS-PAGE gels were ordered from Novex. Reagents for synthesis of oligonucleotides were from Applied Biosystems. All other chemicals were ordered from Sigma chemical company and were of reagent grade or better.

Synthesis and cloning of the gene coding for the Neurospora crassa metallothionein into pMal-c and pMal-p expression plasmids:

Oligonucleotides were synthesized (0.2 µM scale) on an Applied Biosystems 371 DNA synthesizer. Four overlapping oligonucleotides were synthesized with the sequences shown below (for details see FIG. 1A and FIG. 1B).

NCTOP 1:5' GGTGACTGTGGTTGTTCTGGTGCCTCT-TCTTGTAACTGTGGTTCTGGC 3' [SEQ ID NO:3]

NCTOP 2:5' TGTTCTTGTTCTAACTGTGGCTCTAAAT-GATAACTGCA 3' [SEQ ID NO:4]

NCBOT 1:5' ACAGTTACAAGAAGAGGCACCAGAA-CAACCACAGTCACC 3' [SEQ ID NO:5]

NCBOT 2:5' GTTATCATTTAGAGCCACAGTTAGAA-CAAGAACAGCCAGAACC 3' [SEQ ID NO:6]

Oligonucleotides were purified by running on a 20% polyacrylamide gel and then eluting them from excised gel slices using an Elutrap device. Oligonucleotides were phosphorylated and subsequently ligated to each other and to the expression plasmids pMal-c and pMal-p using standard molecular biology protocols (Maniatis et al., *Molecular cloning*: a laboratory manual. Cold Spring Harbor Laboratory, Cold Spring Harbor, N.Y. (1982), the entirety of which is incorporated herein by reference for all purposes). The ligated expression plasmids were transformed into *E. coli* TB1 bacterial cells and characterized as detailed below.

Expression of the maltose binding protein-Neurospora crassa metallothionein recombinant protein:

*E. coli* strain TB1 was transformed with the pMal-c and pMal-p expression vectors to provide recombinant bacterial strains NCC and NCP respectively. Bacterial cultures containing the expression plasmids as well as cultures not containing the plasmids (as negative control) were grown in Luria broth at 37° C. to an OD of 0.6 measured at 600 nm wavelength and were subsequently induced with IPTG (isopropyl-β-D-thio-galactopyranoside) at a concentration of 2 mM for 1 hour. The cells were subsequently harvested and used for purification of the NCC and NCP proteins or for cadmium uptake experiments as described below.

DNA and protein sequence analysis:

DNA sequencing of the expression plasmid was carried out using an Applied Biosystems DNA sequencer. Amino acid analysis was performed on the purified NCC and NCP proteins by Baylor College of Medicine Protein Sequencing Facility, Houston, Tex.

Cell fractionation and purification of the NCC and NCP proteins.

Cell fractionation of the bacterial cells into periplasmic and cytoplasmic fractions was achieved by the cold osmotic shock procedure (Neu et al., *J. Biol. Chem.* 240:3685–3692 (1965), the entirety of which is incorporated herein by reference for all purposes). Briefly, the bacterial cells (from 100 mls of induced culture) were resuspended in 20 mls of 0.5M Tris-HCl pH 7.5, 0.005M EDTA, and 20% sucrose and shaken at room temperature for 10 min. The cells were then pelleted, resuspended in 5 mM MgSO$_4$ and stirred on ice for 10 min. The cells were subsequently pelleted and the supernate containing the periplasmic proteins was stored for further purification. The pellet was resuspended in 20 mls of 0.05M Tris-HCl pH 7.5, 0.005M EDTA and lysozyme was added at a concentration of 0.2 mg/ml and the sample was left on ice for 30 min. DNAase was added to reduce the viscosity and the sample was centrifuged in a Sorval SS34 rotor at a speed of 15,000 RPM. The supernate containing cytosolic proteins was stored for further purification. The maltose binding protein-metallothionein fusion protein was purified from either the periplasmic or cytosolic fractions by affinity chromatography using amylose affinity resin as described by the manufacturer (New England Biolabs).

Sodium dodecyl sulphate-polyacrylamide gel electrophoresis (SDS-PAGE):

This was performed essentially as described by Laemmli UK, *Nature London* 227:680–685 (1970), the entirety of which is incorporated herein by reference for all purposes. Bacteria containing either the pMal-c or the pMal-p expression vectors were grown and induced with isopropyl-β-thiogalactoside. The bacteria were fractionated into periplasmic and cytoplasmic fractions. The protein sample was dissolved in solubilization buffer containing 50 mM Tris-HCl, pH 7.5, 3% SDS, 1.7M 2-mercaptoethanol and 20% (w/v) glycerol, and boiled for 3 min. Samples were then loaded on precast 4–20% gels and electrophoresed at 30 mA (constant current) Following electrophoresis, samples were stained with 0.1% Coommassie blue in 50% (v/v) methanol for several hours. The gels were destained with several changes in 50% methanol, 10% acetic acid. $^{109}$Cd uptake experiments.

Figure 2:
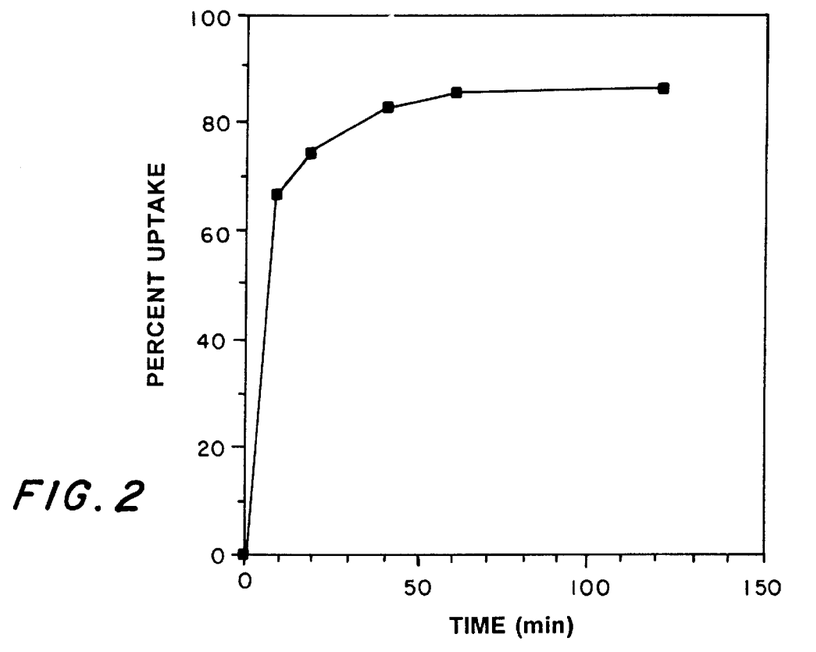
FIG. 2 is a graph showing the time course of cadmium uptake by the NCP bacteria. The NCP bacteria were grown and induced as described in Materials and Methods. Cadmium was added at a final concentration of 0.2 $\mu$M and, at the times indicated in the Figure, an aliquot of the sample was removed and centrifuged. Both the supernatant and the pellet were counted to determine percentage uptake by the bacteria. 100% uptake was 1 nmol.
Figure 3:
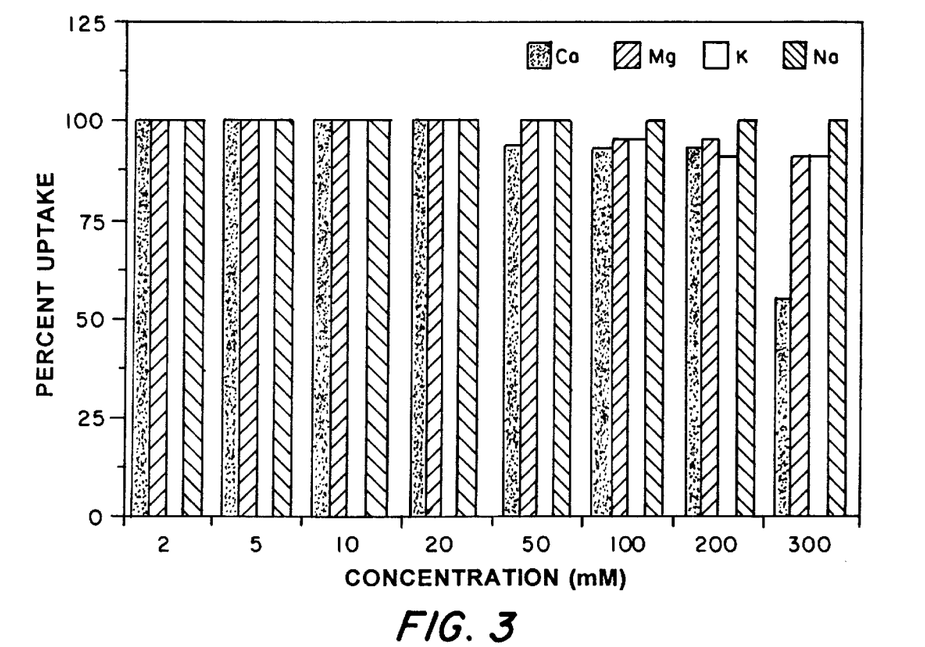
FIG. 3 is a graph showing the effect of various ions on the uptake of cadmium by the NCP bacteria. The NCP bacteria were grown and induced as described in Materials and Methods. Cadmium was added at a final concentration of 0.2 $\mu$M plus the indicated concentrations of calcium, magnesium, sodium, or potassium ions. Incubation was carried out for 1 h after which the sample was centrifuged and the supernatant and pellet were counted to determine percentage uptake by the bacteria; 100% cadmium uptake was uptake of cadmium in the absence of any other ions, which was 0.8 nmol.
Figure 4:
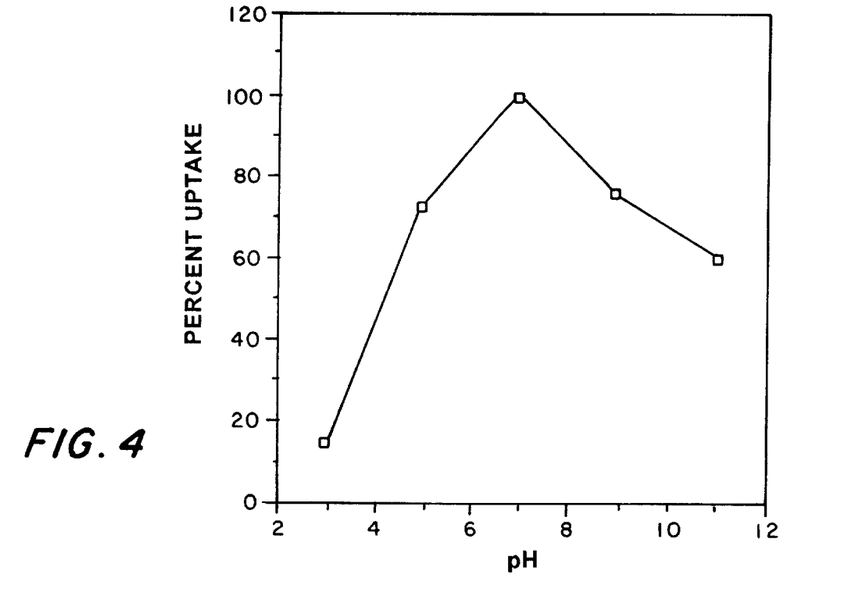
FIG. 4 is a graph showing the pH profile of cadmium uptake by the NCP bacteria. NCP bacteria were grown as described in Materials and Methods. The bacteria were resuspended in buffers ranging in pH from 3.0 to 11.0. (see Materials and Methods). Incubation was carried out for 1 h, after which the sample was centrifuged and the supernatant and pellet were counted to determine percentage uptake by the bacteria; 100% activity was uptake at pH 7.0, which was 0.8 nmol.

Three stock solutions of cadmium chloride were prepared by addition of 0.5 µCi of radioisotopic $^{109}$Cd (specific activity 180 Ci/mole) to three 5 ml aliquots of cold cadmium chloride with concentrations of 20 µM, 100 µM, and 1 mM and specific activities of 5 mCi/mole, 1 mCi/mole, and 0.1 mCi/mole respectively. Bacterial cultures (TB1, NCC, NCP) were grown and induced as described above. After induction with IPTG, 5 mls of the bacteria (corresponding to approximately 4×10$^9$ cells) were pelleted and washed once with 0.1M Tris-HCl pH=7.0. The bacteria were resuspended in 5 mls of the same buffer and 50 µl of each stock solution of cadmium chloride was added to the samples giving a concentration of 0.2 µM, 1 µM, or 10 µM cadmium chloride in the samples as indicated in the figures or Table 2. Incubations were carried out for 1 hour at 37° C. unless stated otherwise in the figures (FIG. 2). The bacteria were subsequently pelleted and aliquots of the supernate and the bacterial pellet were then counted and $^{109}$Cd uptake was determined. All samples were counted using a Packard liquid scintillation counter which measured the X-ray produced by $^{109}$Cd with an efficiency of about 40%. For pH studies bacteria were resuspended in 5 mls of one of the following buffers: 0.1M sodium acetate pH=3.0, 0.1M sodium acetate pH=5.0, 0.1M Tris-HCl pH=7.0, 0.1M Tris-HCl pH=9.0, or 0.1M Tris pH=11.0. With the exception of the results presented in Table 2 all other cadmium uptake experiments were performed with cadmium concentration of 0.2 µM in the sample mix (FIGS. 2, 3 and 4).

RESULTS

Synthesis and cloning of the *Neurospora crassa* metallothionein gene into the pMal-c and pMal-p expression vectors.

Heterologous protein expression in bacteria often results in the rapid degradation of the expressed protein (especially in the case of low molecular weight proteins) or results in the formation of insoluble inclusion bodies which render the protein nonfunctional inside the cell and requires harsh treatment for its extraction and purification from the bacteria (Ivanov et al., *Gene* 59:223–230 (1987), the entirety of which is incorporated herein by reference for all purposes). The metallothionein gene from various sources has been expressed in *E. coli*, but in several of these cases it has been found that the protein does not accumulate to an appreciable amount and has a very short half life (Murooka et al. *Appl. Environ. Microbiol.* 53:204–207 (1987). These problems have been circumvented by expressing the metallothionein gene as fusion proteins (Mbikay et al., *DNA* 2:23–30 (1983), the entirety of which is incorporated herein by reference for all purposes; Romeyer et al., *Journal of Biotechnology* 8:207–220 (1988), the entirety of which is incorporated herein by reference for all purposes; Romeyer et al., *Applied and Environmental Microbiology* 56:2748–2754 (1990), the entirety of which is incorporated herein by reference for all purposes). For the present studies, the Neurospora crassa metallothionein gene was fused with the maltose binding protein gene and two constructs were made, one which produces the protein in the cytosol and the other which targets the protein to the periplasm. It was anticipated that the periplasmic targeted construct would yield a more stable product, as well as rendering the metallothionein fusion product more accessible to cadmium ions.

Figure 1A:
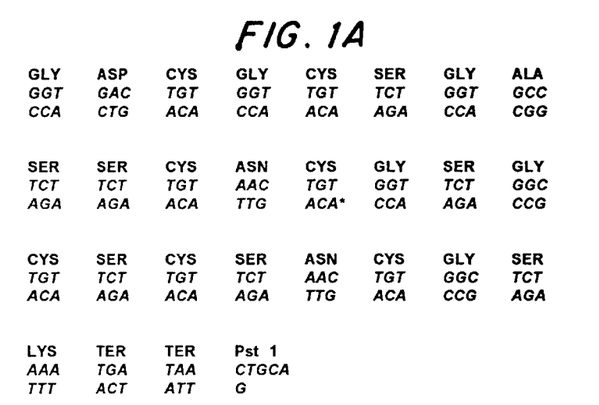
FIG. 1A shows the nucleotide and amino acid sequence of a synthesized metallothionein gene useful in the method of the present invention.
Figure 1B:
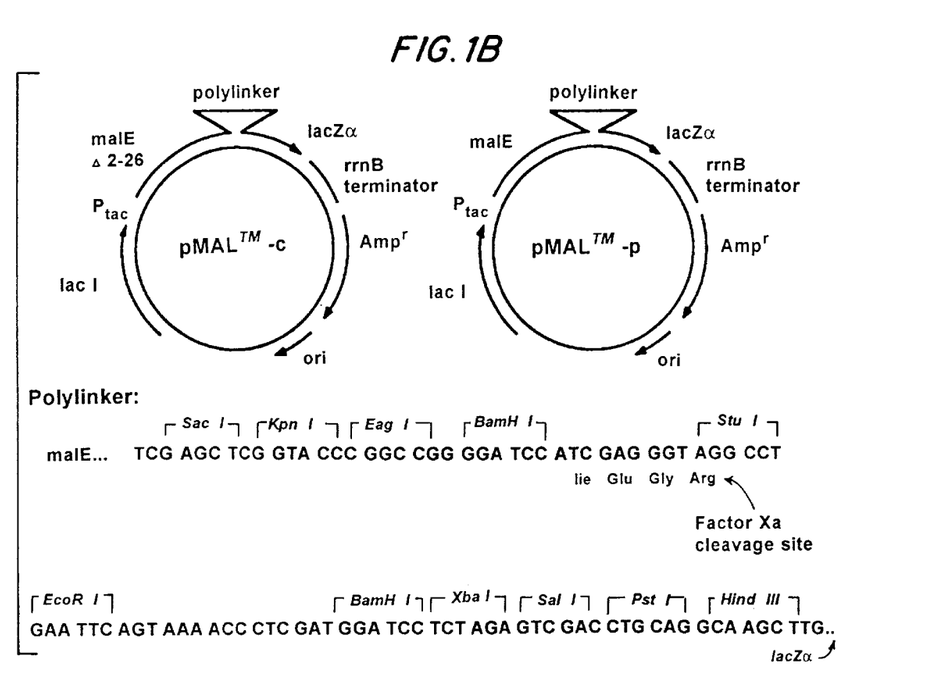
FIG. 1B is a map of the pMal-c and pMal-p expression vectors including the multiple cloning sites.

The strategy used to synthesize and clone the *Neurospora crassa* metallothionein gene into the pMal-c and pMal-p expression vectors is summarized in FIG. 1. This gene which codes for a protein of 25 amino acids was constructed using 4 oligonucleotides (see Materials and Methods section above) and cloned directionally into the expression vectors. The 5' end of the synthesized DNA was blunt-end ligated to the expression vector treated with the restriction enzyme Stu 1. The 3' end of the gene was designed with a Pst 1 overhang which was cloned into the expression vector after treating with the restriction enzyme Pst 1. The synthetic gene was designed with two termination codons at the 3' end to ensure termination of the recombinant gene. Following cloning, the region of the expression vectors containing the *Neurospora crassa* metallothionein gene was sequenced and was found to be exactly as predicted (data not shown).

Expression and localization of the NCC and NCP proteins:

The NCC and NCP bacteria as well as the TB1 (as negative control) were grown and induced with IPTG as described in Materials and Methods. Aliquots of bacterial cells were removed before and after induction with IPTG, mixed with an equal volume of SDS-PAGE solubilization buffer, boiled for 2 minutes, and subjected to SDS-PAGE. Results showed the appearance of a protein band of molecular weight 45 kDa (the expected molecular weight of maltose binding protein-*Neurospora crassa* metallothionein fusion protein) upon induction of the NCC and NCP bacteria but not in the TB1 bacteria (results not shown). The 45 kDa protein band was nearly twice as intense for the NCC bacteria as compared to the NCP bacteria. The lower relative yield of the NCP protein is comparable to results obtained from the expression of other proteins using the pMal-p vector (New England Biolabs). To determine the cellular location of the NCC and NCP proteins the bacteria containing the two expression vectors were induced with IPTG and subjected to cell fractionation. Following cell fractionation the recombinant fusion protein was purified from the cytoplasmic and periplasmic fractions of both the NCC and the NCP bacteria and subjected to SDS-PAGE. As shown by SDS-PAGE analysis of periplamic and cyoplasmic fractions from bacteria expresssing the NCC and NCP proteins, almost all of the NCC protein is present in the cytosol whereas the majority of the NCP protein is located in the periplasm. B-galactosidase activity assay was performed on the cytoplasmic and periplasmic fractions of the NCC and NCP transformants and only the cytoplasmic fraction was found to contain B-galactosidase activity, demonstrating that no cytoplasmic proteins had leaked into the periplasmic fraction during cell fractionation. To confirm the authenticity of the NCC and NCP fusion proteins, purified samples were subjected to amino acid composition analysis. As shown in Table 1, the theoretical sum of the maltose binding protein and *Neurospora crassa* metallothionein amino acid composition compares very well with the actual amino acid composition. Of particular significance is the fact that maltose binding protein contains no cysteine (Duplay et al. *J. Biol. Chem.* 259:10606–10613 (1984), the entirety of which is incorporated herein by reference for all purposes) whereas the recombinant protein contains 1.4 mole percent of cysteine reflecting the addition of the metallothionein protein which has 7 cysteines to the maltose binding protein.

TABLE 1

Amino acid composition of the MBP-NCP recombinant protein (MBP-NCP maltose-binding-protein-*N.-crassa*-protein, Asx Asp + Asn, Glx Glu + Gln, NP not performed)

| Amino acid | MBP (mol %) calculated | MBP-NCP (mol %) calculated | MBP-NCP (mol %) observed |
|---|---|---|---|
| Ala | 12.1 | 11.7 | 11.4 |
| Arg | 1.6 | 1.5 | 1.6 |
| Asx | 12.3 | 11.8 | 12.8 |
| Cys | 0.0 | 1.7 | 1.5 |
| Glx | 9.8 | 9.2 | 9.2 |
| Gly | 7.9 | 8.6 | 9.1 |
| His | 0.8 | 0.7 | 0.7 |
| Ile | 6.5 | 6.1 | 6.0 |
| Leu | 8.2 | 7.6 | 7.6 |
| Lys | 9.8 | 9.4 | 8.8 |
| Met | 1.6 | 1.5 | 1.1 |
| Phe | 4.1 | 3.8 | 4.0 |
| Pro | 5.7 | 5.3 | 6.3 |
| Ser | 3.3 | 4.8 | 5.8 |
| Thr | 5.4 | 5.1 | 5.0 |
| Trp | 1.9 | 1.7 | NP |
| Tyr | 3.8 | 3.6 | 3.6 |
| Val | 4.9 | 4.5 | 5.3 |

$^{109}$Cd uptake experiments:

Although bacteria expressing various metallothionein genes have previously been shown to accumulate considerably more heavy metal than control bacteria these studies were performed under conditions where the bacteria were grown in the presence of the heavy metal (Berka et al., *J. Bacteriol.* 170:21–26 (1988), the entirety of which is incorporated herein by reference for all purposes; Romeyer et. al. 1988, supra). It is unlikely, however, for genetically engineered bacteria to be able to survive, and accumulate metals in actual waste waters which in addition to the heavy metal contamination may contain other pollutants which can inhibit the growth of the bacteria. Furthermore growth of viable recombinant bacteria often requires the addition of antibiotics (for plasmid maintenance) and inducers (for expression) to the growth media which further complicates their use as bioremedial agents in any significant body of water. The use of genetically engineered bacteria for use as immobilized biomass for biosorption however may be feasible. To this end it is desirable for the bacteria to be able to accumulate the compound of interest (in this case heavy metals) rapidly after the bacteria has grown and been induced to express the protein of interest. To test the ability of the bacteria harboring NCC and NCP proteins to sequester cadmium from solutions, control and recombinant bacteria were grown and induced with IPTG in metal free media and subsequently exposed to various concentrations of $^{109}$Cd ranging from 0.2 $\mu$M (22 ppb) to 10 $\mu$M (1.1 ppm). As shown in Table 2, at all concentrations tested the NCP sequestered significantly more cadmium than the control bacteria. The NCC sequestered less cadmium than the NCP but still considerably more cadmium than the control bacteria. The NCP bacteria was able to reduce the cadmium level of the lowest concentration tested from approximately 22 ppb (0.2 $\mu$M) to less than 5 ppb (0.04 $\mu$M) which is below the National Primary Drinking Water Standards of 10 ppb (*Metal Biosorbents in Bioremediation of Metals Cognis*, Mattison P L (ed), Santa Rosa, Calif. (1992), the entirety of which is incorporated herein by reference for all purposes). The reason for the higher accumulation of cadmium by the NCP bacteria despite a two fold lower expression level than the NCC bacteria is not entirely clear but may be due to possible degradation of the NCC protein inside the cytosol as mentioned earlier.

TABLE 2

Accumulation of cadmium by control and recombinant bacteria. Results represent the accumulation by $4 \times 10^9$ cells. Incubation was for 1 h at 37° C. Numbers in parentheses indicate the total CdCl$_2$ uptake by bacteria.

| Strain | 0.2 $\mu$M CdCl$_2$ uptake | 1.0 $\mu$M CdCl$_2$ uptake | 10.0 $\mu$M CdCl$_2$ uptake |
| --- | --- | --- | --- |
| TBI | 8.2 ± 1.2 (0.08) | 2.6 ± 0.4 (0.13) | 2.5 ± 0.5 (1.25) |
| NCC | 28.5 ± 3.5 (0.28) | 13.0 ± 2.0 (0.65) | 18.5 ± 3.5 (9.25) |
| NCP | 79.0 ± 2.0 (0.79) | 75.0 ± 3.7 (3.75) | 38.5 ± 0.5 (19.00) |

One of the desired properties of a biosorbent is the rapid uptake of metals from solution since this factor determines the time for which the solution needs to be in contact with the biosorbent before metal removal occurs. The time course of cadmium uptake by the NCP bacteria was tested and is shown in FIG. 2. With an initial concentration of 0.2 $\mu$M CdCl$_2$ over 75% of the final uptake capacity was reached within the first 20 minutes of incubation (100% uptake was 1.0 nmoles) although further uptake continued for up to 1 hour. The fast rate of metal uptake by the NCP may have implications for the development of genetically engineered biosorbents since the need for efficient passage of waste water through the biosorbent will probably require the metal binding sites to be near the bacterial cell surface. We are currently in the process of developing cell surface expression strategies.

In addition to heavy metal contamination, waste waters often contain large concentrations of alkaline earth metals which are not toxic and need not be removed from the water source (Mattison, supra). Although ion exchange resins offer good selectivity towards heavy metals they are not absolute and both metal classes may bind to the ion exchanger and are removed (Mattison, supra). This has the effect of reducing the efficiency of the ion exchanger by loading the binding sites of the ion exchanger with alkaline earth metals which would other wise be used for the uptake of heavy metals. One of the potential advantages of biosorbents is their ability to discriminate between heavy metals and transition earth metals. For example, one of the most selective biosorbents is Algasorb which is an immobilized form of the algae *Chlorella vulgaris*. It has been reported for Algasorb that up to 1000 ppm of calcium (25 mM) and magnesium (40 mM) inhibited the uptake of 0.1 mM copper by about 30% (Darnall et al. *Recovery of heavy metals by immobilized algae*. in R. Thompson ed. TRACE METAL REMOVAL FROM AQUEOUS SOLUTION The Royal Society of Chemistry, London. 1 (1986), the entirety of which is incorporated herein by reference for all purposes). To compare these results with the selectivity of the NCP bacteria, cadmium uptake was tested in the presence of various concentrations of sodium, potassium, calcium, and magnesium. In these experiments the NCP bacteria was grown, induced, and harvested as described in Materials and Methods and then incubated with $^{109}$Cd (0.2 $\mu$M concentration) in the presence of various concentrations of sodium, potassium, calcium, and magnesium. As shown in FIG. 3 the recombinant bacteria retained over 90% of its cadmium binding activity in the presence of concentrations of up to 200 mM of the various ions (100% uptake in the absence of any other ions was 0.8 nmoles). These results demonstrate the exceptional selectivity of the metallothionein for heavy metals (especially copper and cadmium) where a $10^6$ fold excess of the alkaline earth metals failed to inhibit the binding of cadmium to the NCP bacteria.

The pH profile of cadmium uptake by the NCP bacteria is shown in FIG. 4. Maximum uptake is attained at pH of 7.0 with uptake diminishing to 75% of maximum within the pH range of 5–11 and falling below 15% at pH of 3 (100% uptake at pH 7.0 was 0.8 nmoles). The potential of this pH dependent binding for the stripping of metal from the NCP bacteria was tested by loading the NCP bacteria with cadmium at pH 7 and subsequently resuspending the bacteria in pH 3 buffer. Whereas resuspension in pH 3 buffer causes over 85% of the bound cadmium to be stripped off the bacteria and released into the supernatant, resuspension of cadmium loaded NCP in pH 7 buffer results in less than 10% removal of the bound cadmium. Furthermore reincubation of the NCP bacteria in pH 7.0 buffer regenerated over half of the cadmium binding sites and allowed the bacteria to be used for another round of cadmium binding.

EXAMPLE 2

Heavy metal uptake

Procedures

Growth and Expression of the NCP. Growth and expression of the NCP was done as described in the Materials and Methods section of Example 1, above.

Heavy metal uptake experiments: Heavy metal uptake experiments were performed using free cells except for the experiments performed in FIG. 5 which used cells encapsulated in either alginate or acrylamide (see below). The experiments in Table 3 were performed using non radioactive heavy metals at the concentrations indicated. All other experiments were performed using $^{109}$Cd at a final concentration of 1 $\mu$M with a specific activity of 1 mCi/mol. All incubations were carried out for 1 hour at room temperature. Testing the effect of NaN$_3$ on the cadmium uptake activity of the NCP was accomplished by pretreating 20 mg of the NCP with 1 mM and 5 mM NaN$_3$ for 1 hour and washing of the cells twice with 50 mM Tris-HCl pH 7.0 prior to cadmium uptake assay. Heat treatment of the NCP was performed by either autoclaving 20 mg of NCP or incubating it at 100° C. for 1 hour prior to $^{109}$Cd uptake assay. Testing the effect of solvents and polyaromatic hydrocarbons was performed by co-incubating each compound at various concentration with 20 mg NCP during $^{109}$Cd assay. Experiments testing the reusability of the NCP (Table 4) were performed using 100 mg of NCP since these experiments involved several cycles of bacterial resuspension and centrifugation. Following a 1 hour incubation, the bound $^{109}$Cd was stripped from the NCP by treatment with either 50 mM NaOAC pH 5.0 or 5 mM HCl pH 2.0 for 5 minutes. Control samples were treated with 50 mM Tris-HCl for 5 minutes. Regeneration of the metal binding sites on the NCP was performed by resuspending the bacteria with 50 mM Tris-HCl pH 7.0 for 20 minutes. With the exception of $^{109}$Cd, which was detected using a Packard liquid-scintillation counter, the analysis of heavy metals was performed by Accura Analytical Laboratories (Norcoss, Ga.).

Encapsulation of NCP into alginate, and acrylamide: The harvested NCP bacteria was aliquoted into 5 mg, 10 mg, 50 mg, and 100 mg, wet weight portions, resuspended in 1 ml of 50 mM Tris-HCl pH 7, and encapsulated as follows. For alginate encapsulation, the samples were added to 1 ml of 2% sodium alginate (1% final concentration). Controls were comprised of only Tris buffer and alginate. Utilizing a 5 cc syringe, each sample was slowly extruded through an 18 gauge needle into 35 ml of 200 mM calcium chloride. The alginate beads which were formed in the calcium chloride solution at room temperature were recovered, washed in Tris buffer and used for $^{109}$Cd uptake experiments. For acrylamide encapsulation the samples were mixed with 1 ml of 20% polyacrylamide solution and 10 $\mu$l of 25% ammonium persulfate to yield a final 10% polyacrylamide concentration. Polymerization was initiated by the addition of 10 $\mu$l of N,N,N',N'-tetramethyl ethylenediamine and the sample was left at 25° C. for 1 hour for complete polymerization. Controls consisted of buffer and acrylamide. The polymerized samples were crushed using a mortar and pestle, washed with Tris buffer and used for $^{109}$Cd uptake experiments.

RESULTS AND DISCUSSION

To test the ability of the NCP to sequester other heavy metals, it was tested for uptake using several environmentally significant heavy metals and the results of these experiments are shown in Table 3. As indicated, the NCP accumulated mercury and lead most efficiently, followed by cadmium, zinc, nickel, and copper which were accumulated to some extent. Chromium was not accumulated. The ability of the NCP to sequester very low concentrations of a broad range of heavy metals from solutions demonstrates the potential utility of the NCP to be used for polishing applications in waste waters containing several heavy metals. Alternative strategies, including expression of other metal binding peptide sequences and modified metallothionein proteins are being studied in order to develop biosorbents with high affinity for metals such as chromium.

TABLE 3

Uptake of various heavy metals by the NCP

| Heavy Metal | NCP0 | NCP10 | NCP20 |
|---|---|---|---|
| | | Concentration (mg/l) | |
| Cadmium | 0.72 ± 0.01 | 0.43 ± 0.03 | 0.31 ± 0.04 |
| Mercury | 0.59 ± 0.05 | 0.15 ± 0.01 | 0.11 ± 0.01 |
| Chromium | 0.56 ± 0.02 | 0.56 ± 0.04 | 0.54 ± 0.04 |
| Lead | 0.47 ± 0.02 | 0.16 ± 0.02 | 0.07 ± 0.01 |
| Zinc | 0.68 ± 0.04 | 0.43 ± 0.06 | 0.36 ± 0.02 |

TABLE 3-continued

Uptake of various heavy metals by the NCP

| Heavy Metal | NCP0 | NCP10 | NCP20 |
|---|---|---|---|
| | | Concentration (mg/l) | |
| Nickel | 0.65 ± 0.01 | 0.50 ± 0.01 | 0.42 ± 0.01 |
| Copper | 0.75 ± 0.03 | 0.67 ± 0.02 | 0.62 ± 0.01 |

*Non radioactive heavy metals were used at the concentrations indicated for NCP0. NCP0 = no NCP added (initial heavy metal concentration); NCP10 = 10 mg NCP; NCP20 = 20 mg NCP.
The indicated amount of NCP and heavy metals were incubated for 1 hr at 25° C. after which the samples were centrifuged and the heavy metal content of the supernatant determined.

To investigate the potential of the NCP to be used repeatedly as a heavy metal biosorbent, it was subjected to several cycles of $^{109}$Cd binding, stripping with dilute acid (50 mM sodium acetate pH 5.0 or 5 mM HCl pH 2.0), regeneration of the binding sites by resuspension of the cells in Tris buffer pH 7.0, and subsequent $^{109}$Cd binding. As shown in Table 4, treatment of $^{109}$Cd loaded NCP with HCl completely removed the bound cadmium from the NCP binding sites (recovery 1).

Results in Table 4 are reported as % uptake and recovery of $^{109}$Cd. Results are average of two experiments with the range indicated. 100 mg wet weight of NCP was incubated with a 1 $\mu$M concentration of $^{109}$Cd for 1 hr at 25° C. Following incubation, the samples were centrifuged and the supernatant counted for radioactivity to determine % uptake Recovery of $^{109}$Cd from the NCP cell pellet was performed by resuspension and incubation of the NCP in the buffers indicated above for 5 min, after which the samples were centrifuged and the supernatant counted to determine % recovery (% of total bound $^{109}$Cd that was eluted from the NCP). Regeneration of the binding sites was accomplished by resuspension of the NCP cell pellet in Tris buffer pH 7.0 for 20 min. Following this incubation the samples were centrifuged, and the NCP was resuspended in Tris buffer containing $^{109}$Cd for a subsequent cycle of metal binding.

TABLE 4

Uptake and recovery of $^{109}$Cd by the NCP

| | Recovery Buffer | | |
|---|---|---|---|
| | Tris | NAOAC | HCL |
| Uptake 1 | 94.5 ± 0.5 | 93.0 ± 0.0 | 86.0 ± 6.0 |
| Recovery 1 | 2.7 ± 0.1 | 14.9 ± 1.7 | 63.6 ± 6.6 |
| Pellet 1* | 97.3 ± 0.1 | 85.1 ± 1.7 | 6.4 ± 6.6 |
| Uptake 2 | 87.0 ± 4.0 | 89.5 ± 0.5 | 92.0 ± 4.0 |
| Recovery 2 | 5.5 ± 0.5 | 44.0 ± 2.0 | 90.0 ± 1.7 |
| Pellet 2 | 94.5 ± 0.5 | 56.0 ± 2.0 | 10.0 ± 1.7 |
| Uptake 3 | 97.6 ± 0.3 | 90.1 ± 0.2 | 98.3 ± 0.2 |
| Recovery 3 | 1.9 ± 0.0 | 23.9 ± 0.9 | 95.4 ± 4.6 |
| Pellet 3 | 98.1 ± 0.0 | 76.1 ± 0.9 | 4.6 ± 4.6 |
| Uptake 4 | 94.6 ± 1.4 | 85.4 ± 0.5 | 98.4 ± 0.5 |
| Recovery 4 | 2.6 ± 0.3 | 58.5 ± 1.5 | 104 ± 7.0 |
| Pellet 4 | 97.4 ± 0.3 | 41.5 ± 1.5 | 0.0 |
| Uptake 5 | 96.4 ± 0.1 | 84.1 ± 0.8 | 98.5 ± 0.0 |
| Recovery 5 | 3.5 ± 0.6 | 53.8 ± 0.4 | 109.4 ± 0.8 |
| Pellet 5 | 96.5 ± 0.6 | 46.2 ± 0.4 | 0.0 |
| Total Pellet Count | 457.0 ± 1.5 | 190.0 ± 1.0 | 43.5 ± 8.7 |

*Results of pellet count are extrapolated from the amount of radioactivity found in the supernatant with the exception of the final pellet count which was determined experimentally. The final pellet count in the total radioactivity present in the cell pellet divided by the radioactivity added to the samples over each of the 5 cycles multiplied by 100 to determine % of total radioactivity present in pellet.

Treatment of the NCP with sodium acetate resulted in some recovery of the bound $^{109}$Cd but HCl appears to be the reagent of choice for the recovery of bound $^{109}$Cd from the NCP. Overall, less than 5% of the bound $^{109}$Cd was eluted in control samples using Tris as an elution buffer indicating that the bound cadmium had not been trapped within the NCP but presumably bound tightly to the metallothionein sites. The results in Table 4 further show that in uptake cycles 2 through 5, all samples were efficient in the subsequent uptake of $^{109}$Cd, indicating that treatment of the cells with HCl or sodium acetate does not result in the loss of the metal binding sites and that repetitive use of the NCP is feasible. Although no appreciable amount of $^{109}$Cd was eluted from the control sample during the recovery 1 cycle, it was still capable of further $^{109}$Cd uptake in cycles 2–5. This is due to the fact that not all of the cadmium binding sites on the NCP were occupied during the first round of $^{109}$Cd binding, thus further uptake continues in these samples. At the conclusion of these experiments, the cell pellets were counted to determine the total $^{109}$Cd bound to the NCP (Table 4, pellet count). The results show that control samples had accumulated an amount of $^{109}$Cd roughly equivalent to the total cadmium which had been added over 5 cycles (indicating no elution of the bound cadmium from the NCP using Tris as elution buffer), whereas the sodium acetate samples contained some bound cadmium (indicating poor elution of cadmium from NCP using sodium acetate) and the HCl treated NCP did not contained low levels of $^{109}$Cd bound to them indicating near complete elution of the bound cadmium from the NCP using HCl. The five cycles of $^{109}$Cd uptake and stripping were performed over a period of 7 days with out any loss in the uptake capacity of the NCP. Long term studies are planned to determine the useful life span of the NCP for heavy metal removal applications.

Often, heavy metal contaminated waste waters are co-contaminated with other toxic compounds and solvents. To determine what effect some of these compounds have on the metal uptake activity of the NCP, $^{109}$Cd uptake by NCP was performed in the presence of selected compounds under varying conditions. There was no inhibitory effect on the $^{109}$Cd uptake activity of the NCP by the following compounds: phenanthrene, naphthalene, fluoranthene, phenol, chloroform and toluene (up to 1000 ppm tested). In addition, heat treatment (100° C. for 1 hr or autoclaving for 20 min) or sodium azide treatment (1 and 5 mM) of the NCP also had no inhibitory effect on the uptake of $^{109}$Cd by the NCP, indicating that metal uptake is metabolism independent and non-viable cells may be used for metal uptake.

Figure 5:
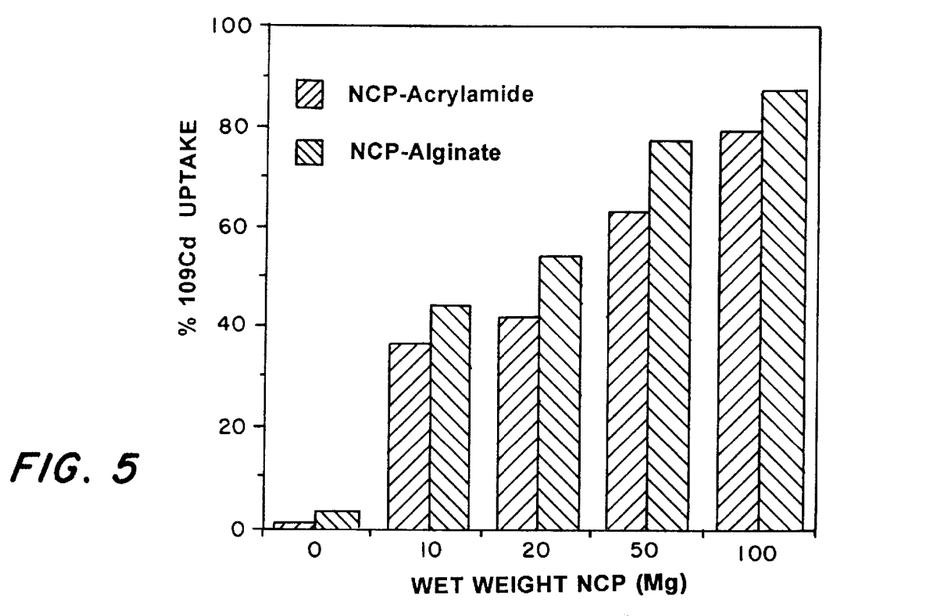
FIG. 5. is a graph of $^{109}$Cd uptake by acrylamide and alginate encapsulated NCP. NCP was encapsulated into acrylamide and alginate as described in Example 2 below. The encapsulated NCP was incubated in 50 mM Tris pH=7.0 buffer containing 1 $\mu$M $^{109}$Cd for 1 hr at 25° C. Following incubation the samples were centrifuged briefly and the supernatant was counted to determine % uptake. Controls of alginate and acrylamide with out any added NCP are indicated by the bars labeled as 0 mg NCP. 100% uptake represents the total radioactivity present in the sample tubes (5.0 nmoles).

Encapsulation of bacteria for waste water treatment offers many advantages over free cells. The use of free bacteria has the disadvantage of having low mechanical strength and difficulty in the separation of the biomass from the effluent. Immobilization of bacteria affords better handling properties to the biosorbent and use of reactors (packed or fluidized) for waste water processing. Drawbacks to immobilization include the potential toxicity of the matrix to be used on the cell. Alginate beads and acrylamide are two of the most popular matrices that have been used for the immobilization of bacteria. As shown in FIG. 5, both acrylamide and alginate immobilized NCP were capable of efficient uptake of $^{109}$Cd from solutions. Alginate or acrylamide alone did not take up any significant amount of $^{109}$Cd from solutions and there were no apparent inhibitory effects from either matrix on the metal uptake activity of the NCP. Packed column operations are being planned to determine which matrix if any will yield acceptable performance for large scale applications. Factors which are important in choosing a matrix for immobilization of a biosorbent include flow rate, elution efficiency, as well as chemical and mechanical stability.

The results presented in this study indicate that the NCP has properties which are desirable and necessary for a heavy metal biosorbent. These properties include affinity for a wide range of heavy metals, reusability and durability, and its potential to be used as non-viable biomass (thus avoiding any regulatory issues involving release of genetically engineered organisms) as well as its ability to be immobilized into a matrix.

Obviously, many modifications and variations of the present invention are possible in light of the above teachings. It is therefore to be understood that, within the scope of the appended claims, the invention may be practiced otherwise than as specifically described.

We claim:

1. A device for removing a heavy metal from an aqueous media, said device comprising a nonviable biomass made of killed bacteria and capable of specifically binding at least one heavy metal, said biomass being covalently attached to a solid support, said killed bacteria having been made by killing recombinant bacteria comprising a bacterial host and a plasmid within said bacterial host, said plasmid being a vector that expresses metallothionein into said periplasmic space of said bacterial host.

2. A device according to claim 1, wherein said bacterial host is *E. Coli.*

3. A device according to claim 1, wherein said plasmid expresses includes a metallothionein gene and expresses said metallothionein gene as a fusion product with a cell membrane protein.

4. A device according to claim 3, wherein said cell membrane protein is a maltose-binding protein.

5. A device according to claim 3, wherein said plasmid is the pMalP expression vector.

6. The device of claim 1, wherein said solid support is an alginate, an acrylamide, or a glass.

7. A method of removing heavy metal contaminants from an aqueous medium, comprising the steps of:

providing a recombinant bacteria, each having a periplasmic space, each of said recombinant bacteria comprising a bacterial host and a plasmid within said bacterial host, said plasmid being a vector that expresses metallothionein into said periplasmic space of said bacterial host;

inducing said recombinant bacteria to express metallothionein into their periplasmic spaces;

killing said induced bacteria to produce a nonviable biomass capable of specifically binding at least one heavy metal;

covalently attaching said biomass to a surface of a solid support;

contacting said surface having said biomass covalently attached thereto with an aqueous medium having at least one heavy metal therein, whereupon said metallothionein specifically binds said at least one heavy metal;

removing said support and said attached biomass from said aqueous medium.

8. A method according to claim 7, wherein said bacterial host is *E. Coli.*

9. A method according to claim 7, wherein said plasmid expresses includes a metallothionein gene and expresses said metallothionein gene as a fusion product with a cell membrane protein.

10. A method according to claim 9, wherein said cell membrane protein is a maltose-binding protein.

11. A method according to claim 9, wherein said plasmid is the pMalP expression vector.

12. The method of claim 7, wherein said specific binding of said at least one heavy metal to said metallothionein is reversible, and further comprising the step of regenerating said biomass by removing said bound at least one heavy metal from said attached biomass.

* * * * *